US00PP23884P3

(12) United States Plant Patent
Goffreda et al.

(10) Patent No.: US PP23,884 P3
(45) Date of Patent: Sep. 10, 2013

(54) PEACH TREE NAMED 'NJ356'

(50) Latin Name: ***Prunus persica* L.**
Varietal Denomination: NJ356

(75) Inventors: Joseph C. Goffreda, Millstone Township, NJ (US); Anna M. Voordeckers, East Windsor Township, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 11 days.

(21) Appl. No.: 13/200,081

(22) Filed: Sep. 16, 2011

(65) Prior Publication Data

US 2013/0074229 P1 Mar. 21, 2013

(51) Int. Cl.
*A01H 5/00* (2006.01)

(52) U.S. Cl.
USPC ..... Plt./198

(58) Field of Classification Search
USPC ..... Plt./197, 195, 198
See application file for complete search history.

*Primary Examiner* — Kent L Bell

(74) *Attorney, Agent, or Firm* — James A. Lucas; Driggs, Hogg, Daugherty & Del Zoppo Co., LPA

(57) ABSTRACT

A new and distinct peach variety of *Prunus persica* named 'NJ356' is provided. This variety is distinguished from other peach varieties by its unique combination of non-showy flowers, fruit that ripen in latter part of the season, attractive fruit with a red blush over a yellow-white ground color, freestone fruit with a juicy, melting texture and low acid flavor, and good production of firm fruit.

6 Drawing Sheets

Latin name of genus and species of the plant claimed: *Prunus persica* L.

Variety denomination: 'NJ356'.

CROSS REFERENCE TO RELATED APLICATIONS

NONE

STATEMENT REGARDING FEDERALLY SPONSORED RESEARCH OR DEVELOPMENT

NONE

BACKGROUND OF THE INVENTION

The present invention relates to a new and distinct variety of peach tree named 'NJ356'. Our new tree resulted from crossing D90-9 as the seed parent with NJ318 peach tree, as the pollen parent. The new variety differs from seed parent D90-9 (unpatented) in that the new variety has small, non-showy flowers and fruit that ripen in the latter part of the season, while the seed parent has large, showy flowers and fruit that do not ripen during a typical growing season. The new variety differs from pollen parent NJ318 (unpatented) in that the new variety ripens two weeks later and produces well colored, firm fruit, while the pollen parent produces fruit that soften rapidly with a low percentage of blush. In comparison to the commercial peach variety 'Snow Giant' (U.S. Plant Pat. No.8,085), the fruit of the new variety has a brighter ground color and matures approximately 10 days earlier. The fruit and leaves of the new variety are also more tolerant to bacterial leaf spot than 'Snow Giant'. The resulting tree was selected when growing in a cultivated area at a fruit research center in Cream Ridge, N.J.

BRIEF SUMMARY OF THE INVENTION

The 'NJ356' variety is distinguished from other peach varieties due to the following unique combination of characteristics:

Attractive round fruit with a depressed, nearly inconspicuous apex point.

Fruit with an attractive red blush over an orange-white ground color.

Good production of firm fruit.

Fruit with a sweet, low acid flavor.

The variety was asexually reproduced at the fruit research center. Asexual reproduction of this new variety by budding onto 'Lovell' rootstock (unpatented) shows that the foregoing characteristics are so reproduced.

The following detailed description concerns the original tree, 'NJ356'. The original tree and asexual progeny have been observed growing in a cultivated area at the research center in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to *The Royal Horticultural Society* (*R.H.S.*) *Colour Chart*. (1966 Edition)

BRIEF DESCRIPTION OF THE DRAWINGS

This new variety is illustrated by the accompanying photographic drawings, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
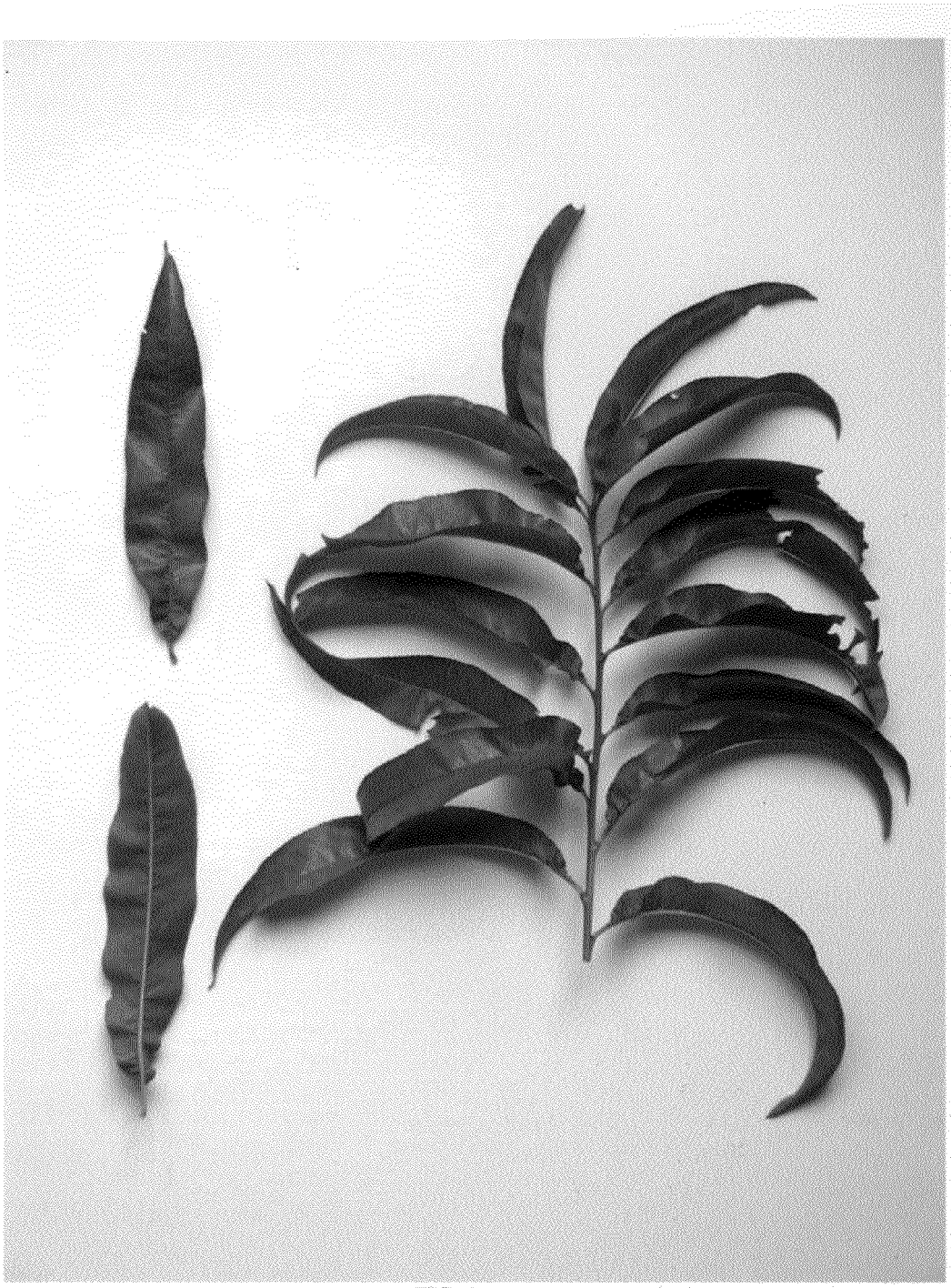
FIG. 1 is a color photograph taken on Aug. 29, 2005 of a characteristic twig of 'NJ356' in late summer bearing typical leaves of the mature foliage.
Figure 2:
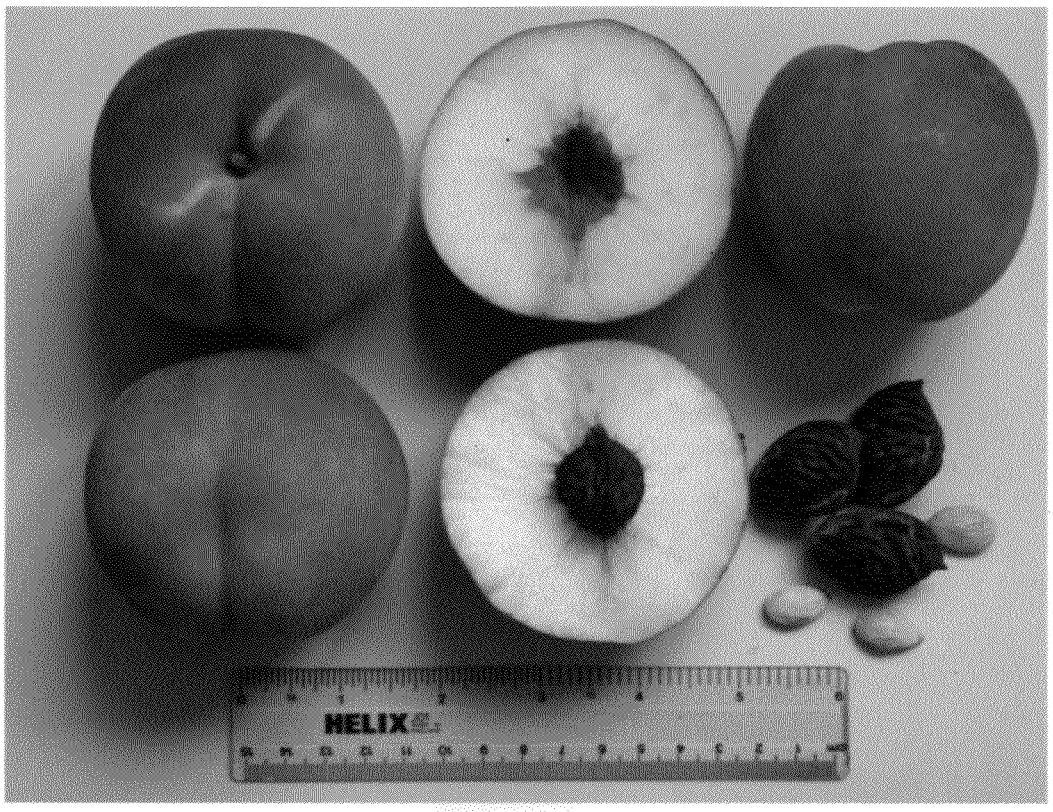
FIG. 2 is a color photograph of mature fruit of 'NJ356' and stones harvested from the fruit research center in Cream Ridge, N.J. on Aug. 24, 2004. Whole fruit are presented in three positions and a transverse cross section to show that the pericarp does not adhere to the pit when the fruit is mature. The stones illustrate the obovoid shape and the pit grooves on the surface of the stone.
Figure 3:
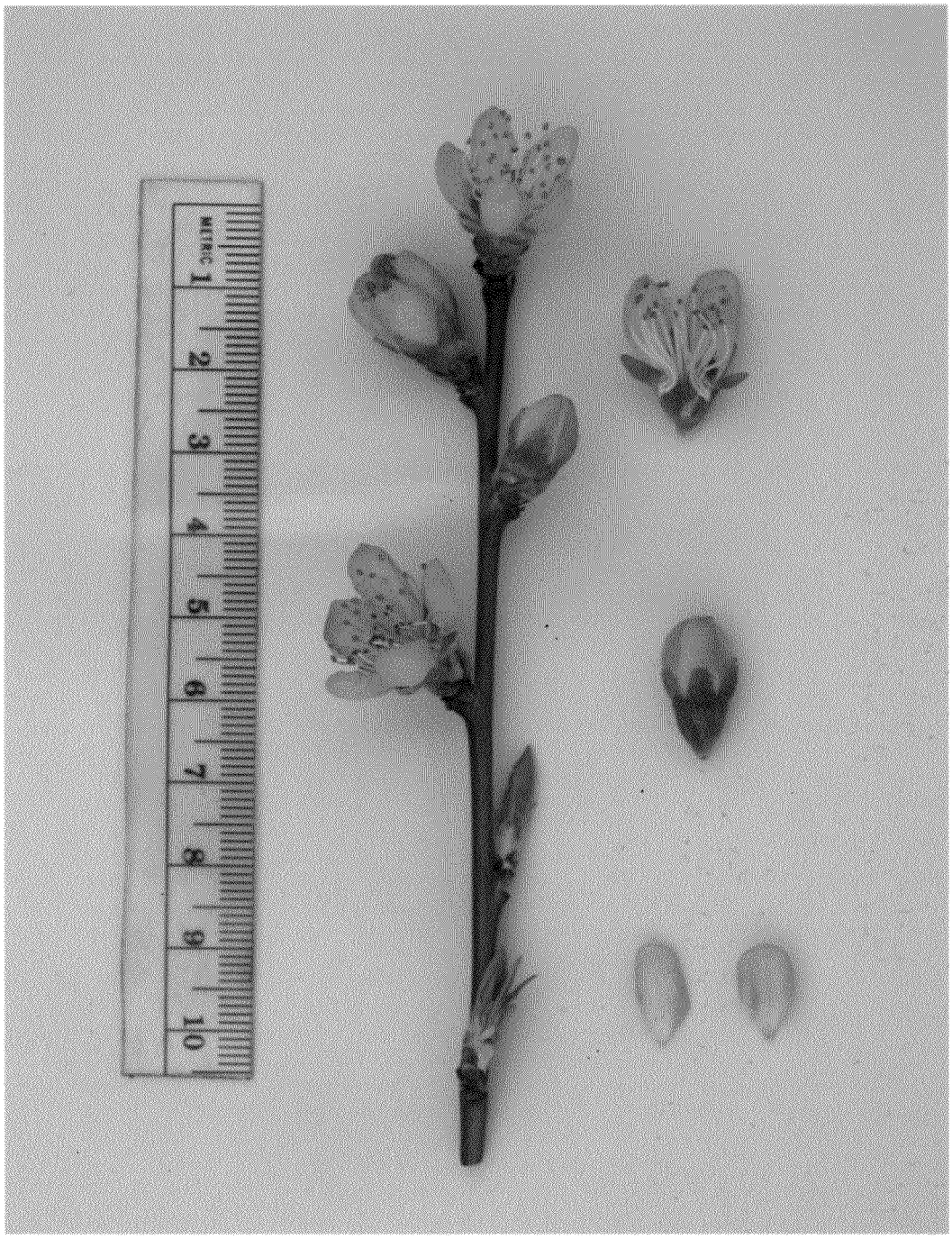
FIG. 3 is a color photograph of a characteristic twig that illustrates the typical flower buds and small, non-showy flowers of 'NJ356' observed on a tree that was 6 years of age on Apr. 21, 2004.
Figure 4:
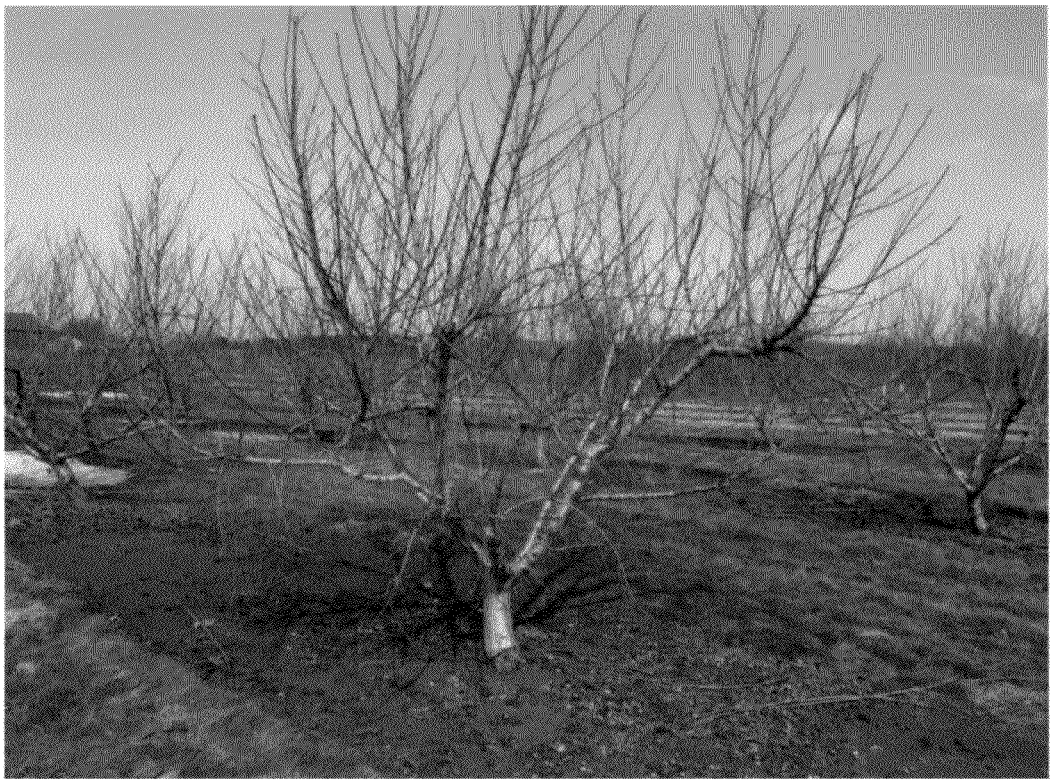
FIG. 4 is a color photograph of a dormant tree of 'NJ356' in late winter, prior to pruning, that illustrates the slight to moderately spreading growth habit of a tree at the fruit research center in Cream Ridge, N.J. on Feb. 17, 2011.
Figure 5:
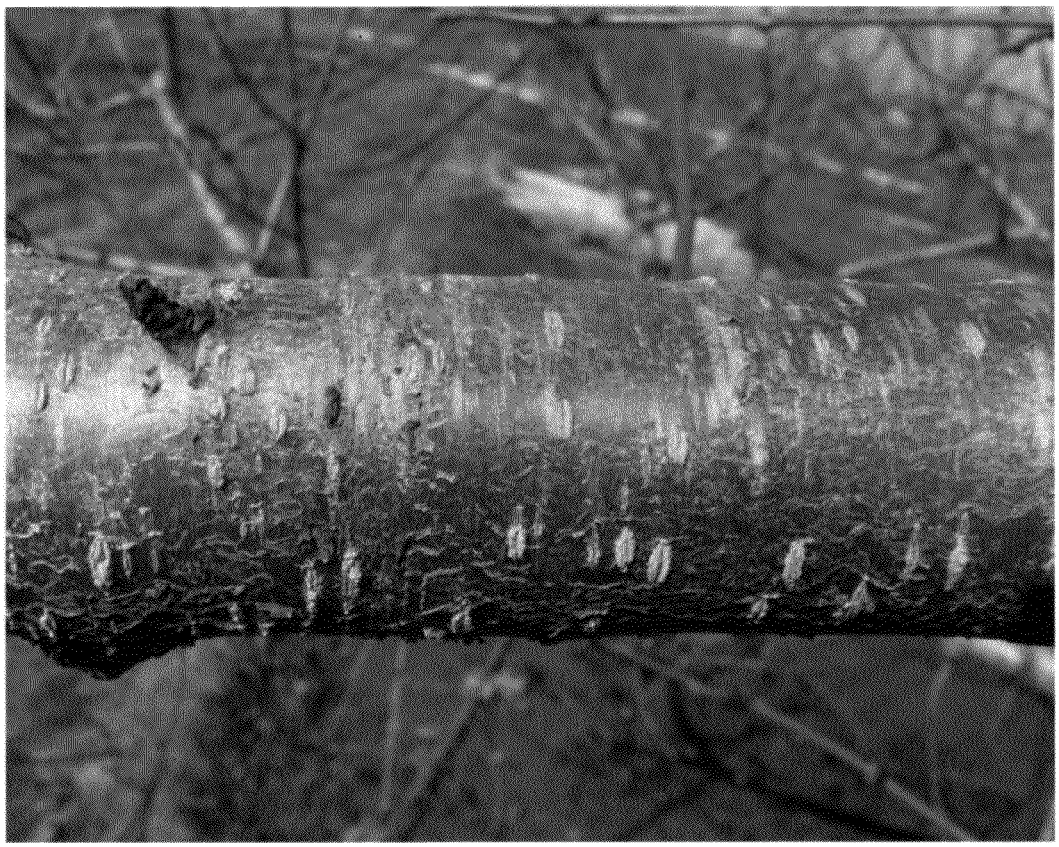
FIG. 5 is a color photograph taken on Feb. 17, 2011 of immature bark of 'NJ356' that illustrates color and the moderate density of grey-brown bordered, elliptical lenticels on the immature bark.
Figure 6:
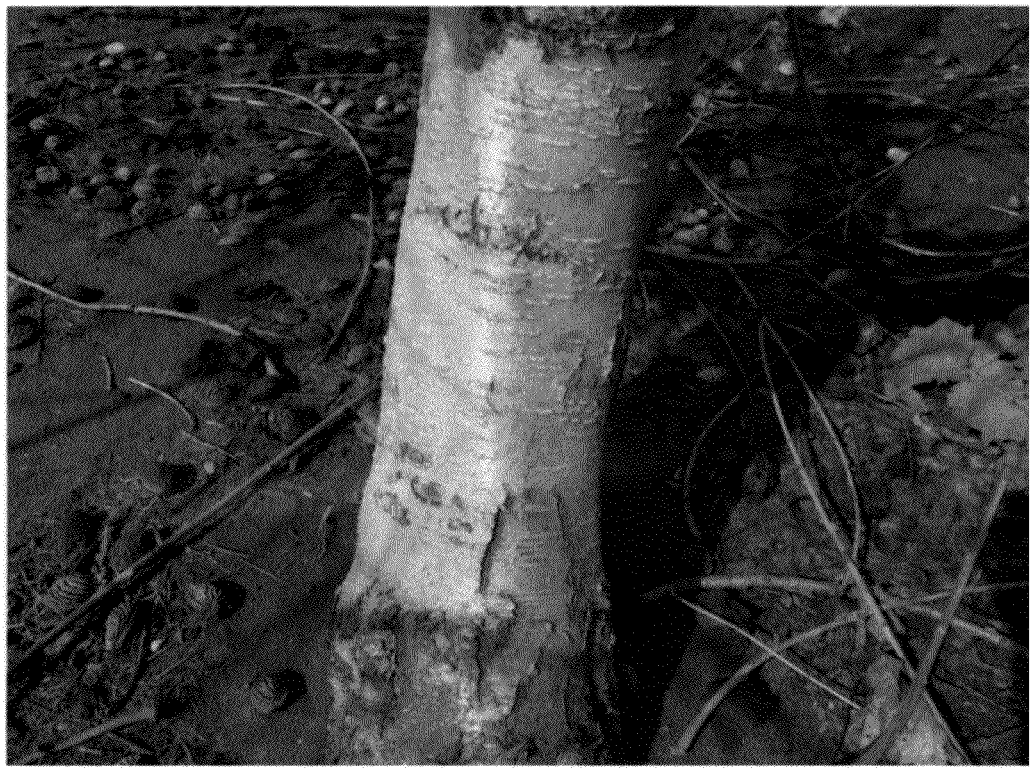
FIG. 6 is a color photograph taken on Feb. 17, 2011 of mature bark of 'NJ356' that illustrates the fairly smooth texture and conspicuous lenticels of the mature bark.

The colors and illustration of this type may vary with lighting and other conditions and, therefore, color characteristics of this new variety should be determined with reference to the observations described herein, rather than from these illustrations alone.

DETAILED BOTANICAL DESCRIPTION

The following detailed description of the 'NJ356' variety is based on observations of an asexually reproduced tree. The observed tree was six years of age and growing on 'Lovell' seedling rootstock (unpatented) in at said fruit research center in Cream Ridge, N.J.

Scientific name: *Prunus persica* L.

Parentage:

*Seed parent*.—D90-9.

*Pollen parent*.—NJ318.

Tree:

*Vigor*.—Vigorous.

*Plant hardiness zone*.—Growth of plants has only been observed in zone 6b.

*Dormant flower bud cold tolerance*.—At least to −20° C.

*Overall shape*.—Slight to moderately spreading.

*Height*.—Average as compared to other peach cultivars. For example, measurement of a typical grafted tree on 'Lovell' seedling rootstock (unpatented) at six years after planting shows an average height of 3.3 meters when grown in Cream Ridge, N.J.

*Width*.—Average as compared to other peach cultivars. For example, measurement of a typical grafted tree on 'Lovell' seedling rootstock (unpatented) at six years after planting shows an average width of 4.3 meters when grown in Cream Ridge, N.J.

*Caliper*.—Six year old tree is 44 cm in circumference measured at 20 cm from the ground.

Trunk and branches:

*Trunk bark texture*.—Fairly smooth with conspicuous lenticels becoming rough as the tree ages.

*Trunk bark color*.—Greyed-green (RHS 197D).

*Primary branches*.—Branches that are approximately 15 cm in circumference are greyed-orange (RHS 177B) in color, overlaid with greyed-green (between RHS 196D to RHS 197D). The branch angles range from 40 to 57 degrees, averaging about 45 degrees.

*Lenticels*.—Moderate density, approximately 2.5 per square cm; lanceolate in shape; typical examples of which measured 3 mm in length and 1 mm in width; greyed-orange (RHS 165C) in color and bordered with greyed-brown (RHS 199D).

*Branch pubescence*.—None.

*New growth bark*.—Color greyed-purple (between RHS 183A and RHS 183B) in sun; color yellow-green (between RHS 152B and RHS 152D) in shade.

*Internodes*.—Length averaging 21.9 mm on a one-year shoot.

Leaves:

*Texture*.—Glabrous.

*Sheen*.—Young leaves semi-glossy with a flat finish on the underside. Adaxial surface of mature leaves is generally smooth, glabrous, and slightly glossy. Abaxial surface of mature leaves is nearly smooth, glabrous, with a matte finish.

*Length*.—About 158 mm to 194 mm, averaging about 180 mm including the petiole.

*Width*.—About 37 mm to 46 mm, averaging about 43 mm.

*Petiole*.—Averaging 10 mm long and about 1.6 mm in diameter.

*Margin*.—Serrulate.

*Margin undulation*.—None to slight.

*Form*.—Lanceolate.

*Apex*.—Acuminate, curved downward.

*Base*.—Cuneate.

*Venation*.—Pinnate.

*Glands*.—Number: About 3 to 5, averaging about 3.4. Position: Located primarily on the leaf margin and petiole. Size: Length averaging 0.9 mm and width averaging 0.7 mm. Form: Reniform.

*Stipules*.—None observed on mature leaves.

*Leaf color*.—Upper leaf surface: Green (between RHS 137B and RHS 137C). Lower leaf surface: Yellow-green (between RHS 147B and RHS 147C). Vein: Yellow-green (RHS 147C).

*Pubescence*.—None.

Flowers:

*Size*.—Small size, typical flower measuring between 14.6 mm to 23.4 mm, averaging about 19.5 mm across.

*Color*.—Dormant bud: Grey to grey-green (between RHS 201A and RHS 195C). Pink stage bud: Red (between RHS 55B and RHS 56C). Open flower: Young open flowers red (between RHS 54C and RHS 54D), with red-purple venation (between RHS 68B and RHS 68C) at petal fall.

*Petals*.—Typically five petals per flower; cupped and obovate in shape; margin entire, averaging about 11.0 mm long and 7.9 mm wide.

*Petal apex*.—Obtuse.

*Petal base*.—Cuneate.

*Stamens*.—Number: Variable, typical range 28 and 36, averaging 32. Length: Variable, between 10.2 mm to 12.6 mm, averaging 10.6 mm. Filament color: Green-white (RHS 157A). Anther color: Red (RHS 46A).

*Pistil*.—Number: One. Size: Length between 16.3 and 19.6 mm, averaging about 17.9 mm. Pistil color: Greyed-yellow (RHS 160A). Ovary: Dense pubescence and ellipsoid in shape.

*Sepals*.—Number: Five. Pubescence: Short and moderate density. Color: Yellow-green (RHS 152B) with a greyed-red (RHS 182B) over color. Shape: Triangular, with a rounded apex. Size: Length averaging 6.2 mm, width averaging 3.8 mm.

*Nectar cup color*.—Yellow (between RHS 7A and RHS 13B).

*Pollen*.—Abundant; yellow (RHS 11A) in color.

*Fragrance*.—Very slight.

*Bloom season*.—Onset of bloom in 2004 on April 16; full bloom on April 19.

Fruit:

*Size*.—Large, averaging about 7.2 cm long, 7.3 cm wide parallel to the suture and 7.6 cm wide perpendicular to the suture.

*Typical weight*.—226 g.

*Form*.—Longitudinal section: Round. Traverse section: Nearly round, one side of suture may tend to be slightly lipped in is some years.

*Suture*.—Shallow, deepening toward the apex.

*Ventral surface*.—Typically smooth, slightly lipped in some years.

*Base*.—Round.

*Apex*.—Fairly flat, apex point very small and depressed.

*Stem*.—Average length of 4.3 mm and an average diameter of 3.6 mm.

*Skin*.—Thickness: Average. Surface: Regular with short pubescence. Tenacity: Average. Astringency: None. Tendency to crack: Low. Color: Mottled red (between RHS 45A and RHS 46A) over a red (RHS 38A) blush; ground color orange-white (between RHS 159A).

*Fruit properties*.—Flesh color: Yellow-white (RHS 158C). Flesh adhesion: Freestone. Juice: Moderate. Texture: Firm, but melting. Fibers: Not noticeable. Ripens: Between August 18 and September 10 at Cream Ridge, N.J. Flavor: Average to above average, low acidity. Soluble solids: Average 12.0%. Aroma: Very slight. Eating quality: Good.

*Keeping quality*.—Average. Has held its flavor and firmness for at least seven days in cold storage at 1° C. to 4° C.

*Shipping quality*.—Very good. Fruit are generally very firm at harvest. No bruising or scaring disorders have been observed.

*Usage*.—Dessert.

*Market*.—Local and long distance.

*Productivity*.—Good. Trees have produced a crop in six out of seven years and a full crop in five out of seven years at Cream Ridge, N.J.

Stone:

*Type*.—Freestone.

*Form*.—Obovoid.

*Base*.—Narrow.

*Apex*.—Medium.

*Surface*.—Pit grooves.

*Ventral suture*.—Medium.

*Dorsal ridge*.—Medium with deep lines.

*External color*.—Greyed-orange (RHS 174B) overlaid with greyed-purple (RHS 183C).

*Internal color when cracked*.—Greyed-orange (RHS 173D).

*Cavity surface color*.—Greyed-orange (between RHS 164B and RHS 164C).

*Average stone dry weight*.—5.4 g.

*Average stone wall thickness*.—Between 4.1 mm along the ventral suture and 10.9 mm at the base.

*Size*.—Averages about 35 mm long, 25 mm wide parallel to the dorsal ridge, and 18 mm wide perpendicular to the dorsal ridge.

*Tendency to split*.—Low.

*Kernel*.—Form: Ovate. Skin color: Greyed-orange (Between RHS 164A and RHS 165B). Vein color: Greyed-orange (between RHS 165A and RHS 165B). Viability: Yes. Size: Averages about 17.6 mm long, 11.0 mm wide, and 3.5 mm in breadth.

Plant/fruit disease and pest resistance/susceptibility: No atypical resistances/susceptibilities have been noted under normal cultural practices.

We claim:

1. A new and distinct variety of peach tree, substantially as herein shown and described.

* * * * *